United States Patent [19]

Mann

[11] Patent Number: 4,637,816

[45] Date of Patent: Jan. 20, 1987

[54] APPARATUS FOR THE ORAL ADMINISTRATION OF CAPSULES TO ANIMALS

[75] Inventor: Derek Mann, Derby, England

[73] Assignee: Dobson Park Industries, PLC, England

[21] Appl. No.: 682,001

[22] PCT Filed: Apr. 26, 1984

[86] PCT No.: PCT/GB84/00143

§ 371 Date: Dec. 12, 1984

§ 102(e) Date: Dec. 12, 1984

[87] PCT Pub. No.: WO84/04239

PCT Pub. Date: Nov. 8, 1984

[30] Foreign Application Priority Data

Apr. 26, 1983 [GB] United Kingdom ................. 8311345

[51] Int. Cl.[4] ................................ A61M 5/18

[52] U.S. Cl. ................................ 604/62; 604/77; 221/197

[58] Field of Search ................................ 604/60, 57-59, 604/61-64, 77; 221/197; 124/45, 48

[56] References Cited

U.S. PATENT DOCUMENTS

| | | | |
|---|---|---|---|
| 453,508 | 6/1891 | Ruby | 604/63 |
| 1,694,246 | 12/1928 | Boyne . | |
| 1,936,437 | 11/1933 | Peters . | |
| 2,017,783 | 10/1935 | Clark . | |
| 2,722,934 | 11/1955 | Brackbill | 604/59 |
| 2,723,661 | 11/1955 | Hull . | |
| 3,192,915 | 7/1965 | Norris et al. . | |
| 3,757,781 | 9/1973 | Smart . | |
| 3,774,607 | 11/1973 | Schmitz . | |
| 3,854,478 | 12/1974 | Cunningham . | |
| 4,004,565 | 1/1977 | Fischer et al. | 604/62 X |
| 4,474,308 | 10/1984 | Bergeron | 604/59 X |

FOREIGN PATENT DOCUMENTS

| | | | |
|---|---|---|---|
| 937399 | 2/1950 | France . | |
| 185616 | 9/1922 | United Kingdom . | |

*Primary Examiner*—Stephen C. Pellegrino
*Attorney, Agent, or Firm*—Kirschstein, Kirschstein, Ottinger & Israel

[57] ABSTRACT

Apparatus for the oral administration of capsules to animals, particularly ruminants such as sheep, comprises a tubular member adapted to be inserted into the animal's mouth so that the tip of the tubular member is near the root of the animal's tongue, means for introducing a capsule into the tubular member and for propelling the capsule to its tip, in which the tip of the tubular member consists of two tip portions extending from the mouth of the tubular member and laterally spaced from one another so as to define a cavity in which a capsule is deposited at the root of the animal's tongue. The top of the tubular member has a convexly curved upper surface adapted to engage the animal's soft palate to encourage a swallowing reaction, and a lower surface shaped to engage and restrain movement of the dorsum and the front part of the animal's tongue. Apparatus is disclosed in which the means for propelling the capsule along the tubular member comprises means for supplying air or gas under pressure to the tubular member. The use of gas to propel the capsule ensures that it is adminstered rapidly with no risk of damage to the animal.

19 Claims, 13 Drawing Figures

APPARATUS FOR THE ORAL ADMINISTRATION OF CAPSULES TO ANIMALS

Figure 1:
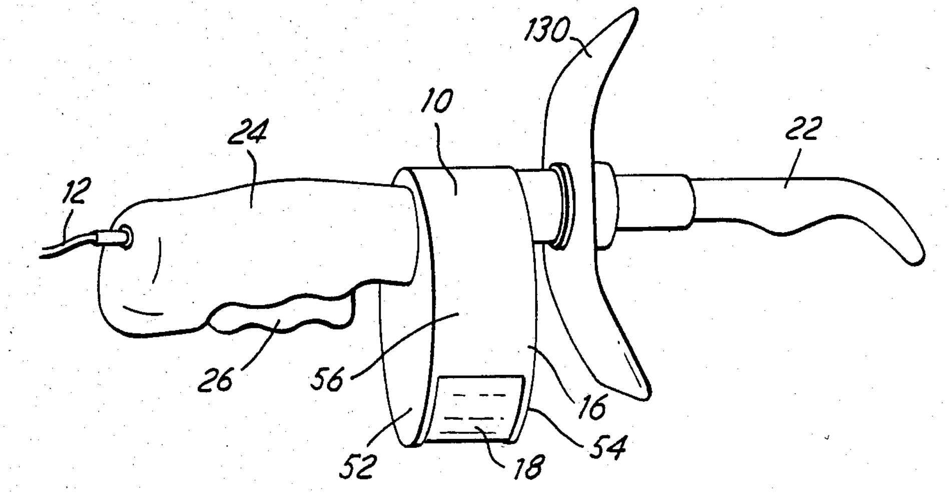

This invention relates to apparatus for the oral administration of capsules to animals.

The invention is more particularly, but not exclusively, concerned with the administration of medicinal capsules to ruminants such as sheep.

There are known balling guns which operate by mechanically pushing the ball or capsule into the animal's throat. This is a slow and tedious process, and involves the risk of damage to the soft parts of the animal's mouth.

There is a need for an apparatus which enables capsules to be administered to animals quickly and easily, and which enables a number of animals to be dealt with in quick succession.

It has been found, by a study of ruminants, and of sheep in particular, that the mechanics and make-up of the animal's mouth gives it great control over anything taken into the mouth. Food taken into the mouth is transported to the throat area by the forward and backward action of the tongue which compresses the food against the hard palate. The hard palate has backwardly inclined ridges which encourage the food to travel backwards towards the throat. The food is collected at the back of the mouth until swallowing occurs. Swallowing is an automatic process caused generally by pressure on the soft palate. The pressure is exerted either by the build up of food at the back of the animal's mouth or by the large hump-like part of the tongue known as the dorsum. Experiment has shown that the ability of a sheep to manipulate its tongue, and the pliability of the soft palate, makes it very difficult to deposit capsules at the back of the sheep's mouth, in a position where the capsule will be swallowed.

This invention includes apparatus for the oral administration of capsules to animals, comprising a tubular member adapted to be inserted into the animal's mouth so that the tip of the tubular member is near the root of the animal's tongue, means for introducing a capsule into the tubular member and for propelling the capsule to its tip, in which the tip of the tubular member consists of two tip portions extending from the mouth of the tubular member and laterally spaced from one another so as to define a cavity in which a capsule is deposited at the root of the animal's tongue.

In one form of the invention, the tubular member is formed at or near its tip with a convexly curved upper surface adapted to engage the animal's soft palate to encourage a swallowing reaction. The tubular member is formed at or near its tip with a lower surface shaped in a concave curve and adapted to engage the dorsum of the animal's tongue to restrain movement of the dorsum. The tubular member may be formed with a second concave surface adjacent the first concave surface and adapted to engage and restrain movement of the front part of the animal's tongue.

Using the apparatus of the invention, the movement of the animal's tongue can be restrained whilst the capsule is deposited into the cavity formed at the base of the animal's tongue and the animal's soft palate is engaged to encourage a swallowing reaction so as to ensure that the capsule is swallowed.

According to another aspect of the invention, there is provided apparatus for the oral administration of capsules to animals, comprising a tubular member adapted to be inserted into the animal's mouth so that the tip of the tubular member is near the root of the animal's tongue, means for introducing a capsule into the tubular member and for supplying air or gas under pressure to the tubular member to propel the capsule to its tip, the tip being shaped to release the capsule into the animal's mouth.

The use of gas, which may be air or a non-toxic gas, to propel the capsule ensures that it is administered rapidly with no risk of damage to the animal.

In one embodiment, the tubular member is part of a hand-held gun including a magazine to hold one or more capsules in a portion in which they can be inserted into the tubular member, and the gun is connected to a source of pressurizing gas through a flexible tube, the supply of gas to the tubular member being controlled by a manually operated valve on the gun. The source of pressurizing gas may be a container carried by a harness secured to the user's body, so that the user has both hands free to hold the animal and the gun.

The magazine may include a cartridge replaceably mounted in a housing forming part of the gun, the cartridge including a rotatable member having a number of circumferentially spaced cavities each adapted to house one capsule, and the rotatable member being rotatable in the housing so that each cavity can be moved in succession to a position in which it can be moved into the tubular member.

Figure 2:
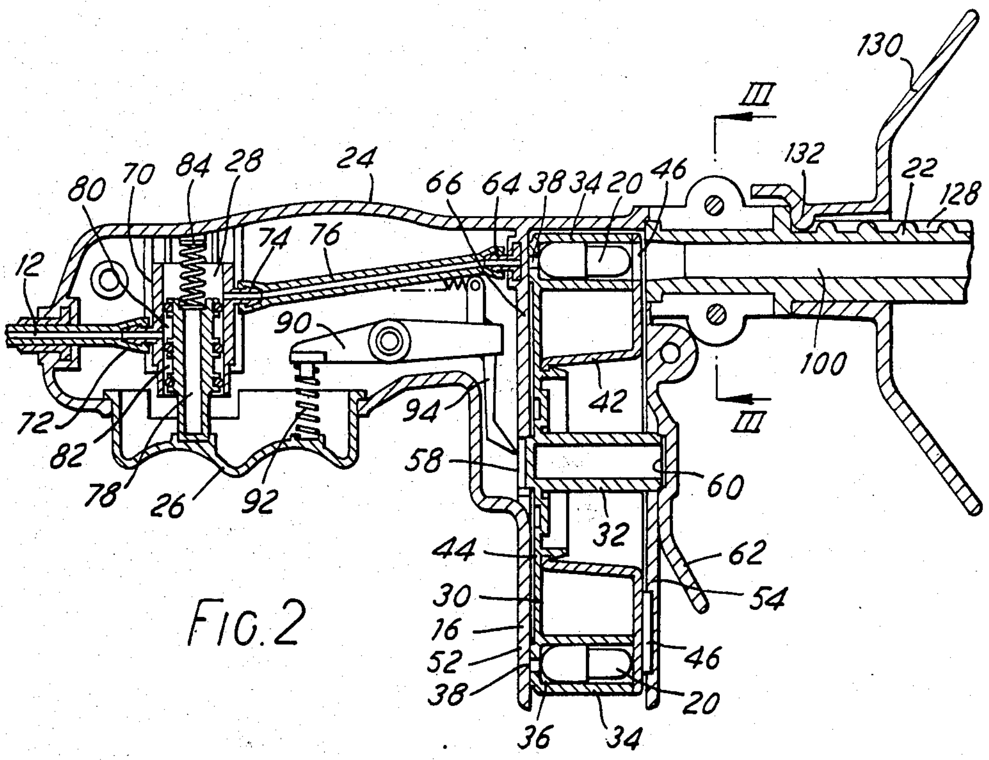
Figure 3:
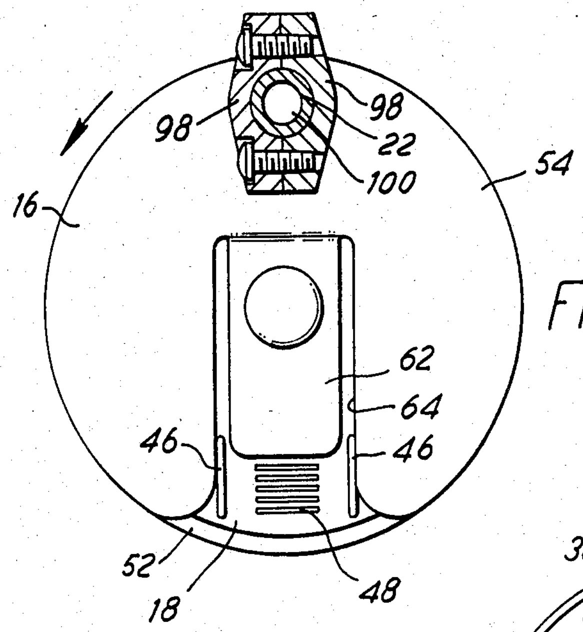
Figure 4:
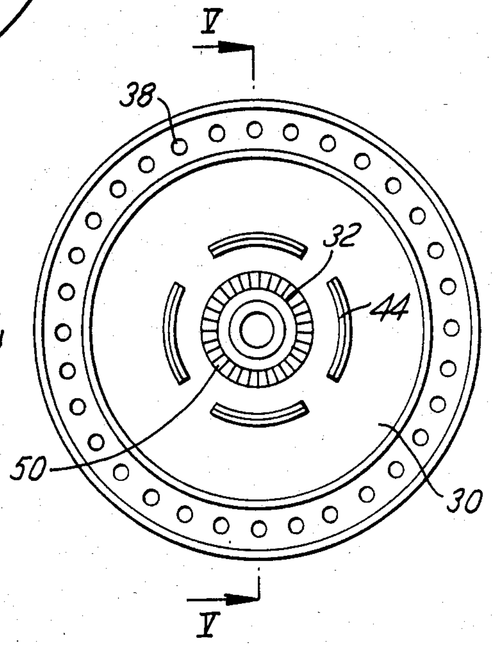
Figure 6:
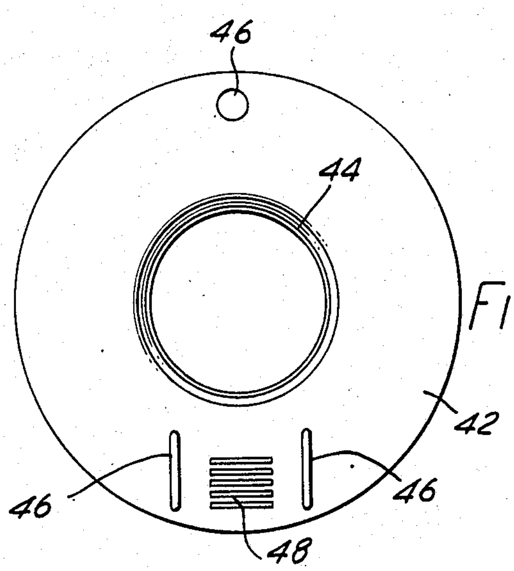
Figure 5:
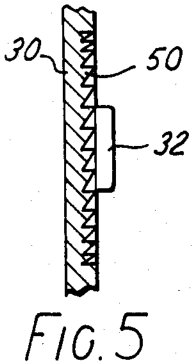
Figure 7:
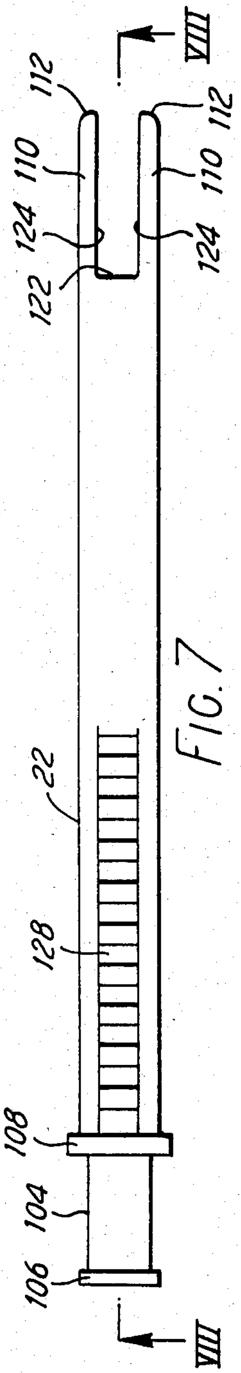
Figure 8:
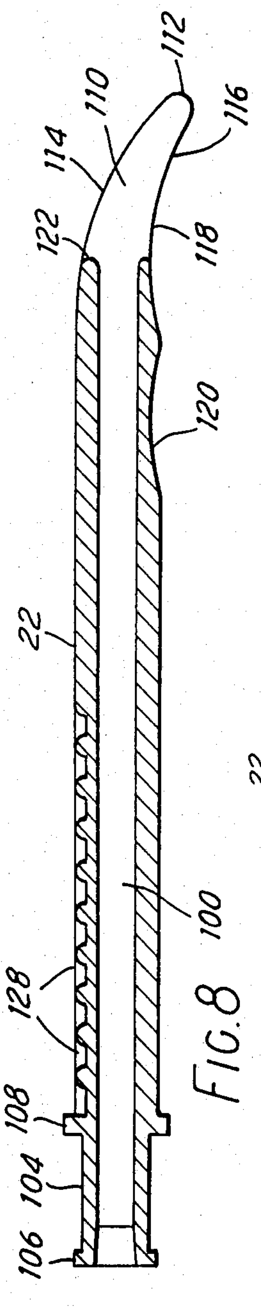
Figure 9:
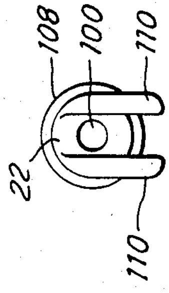
Figure 10:
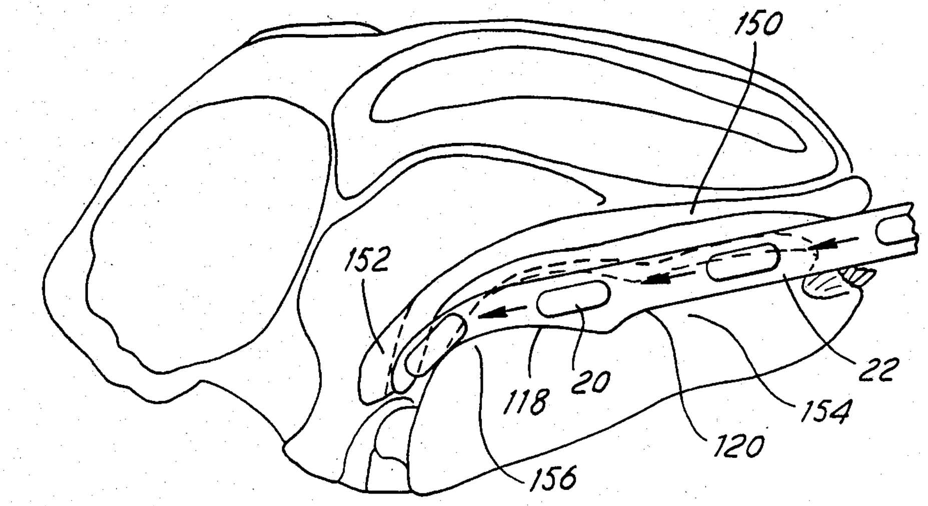
Figure 12:
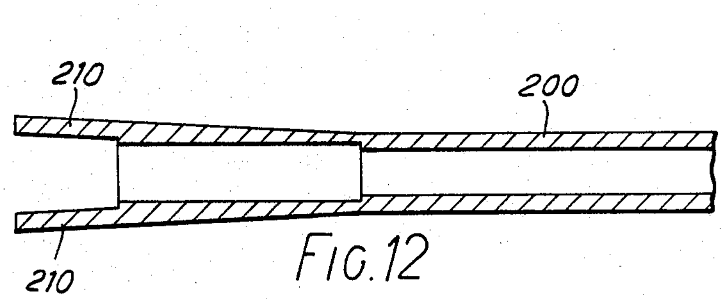
Figure 13:
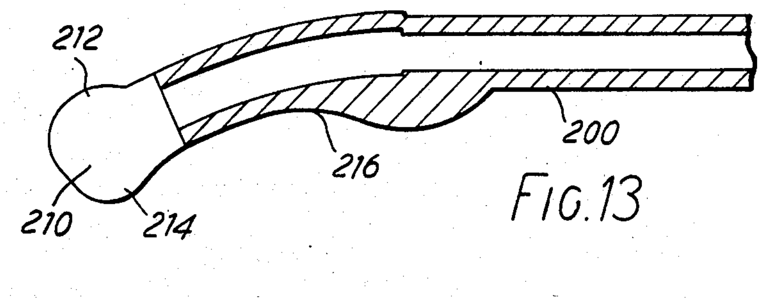
Figure 11:
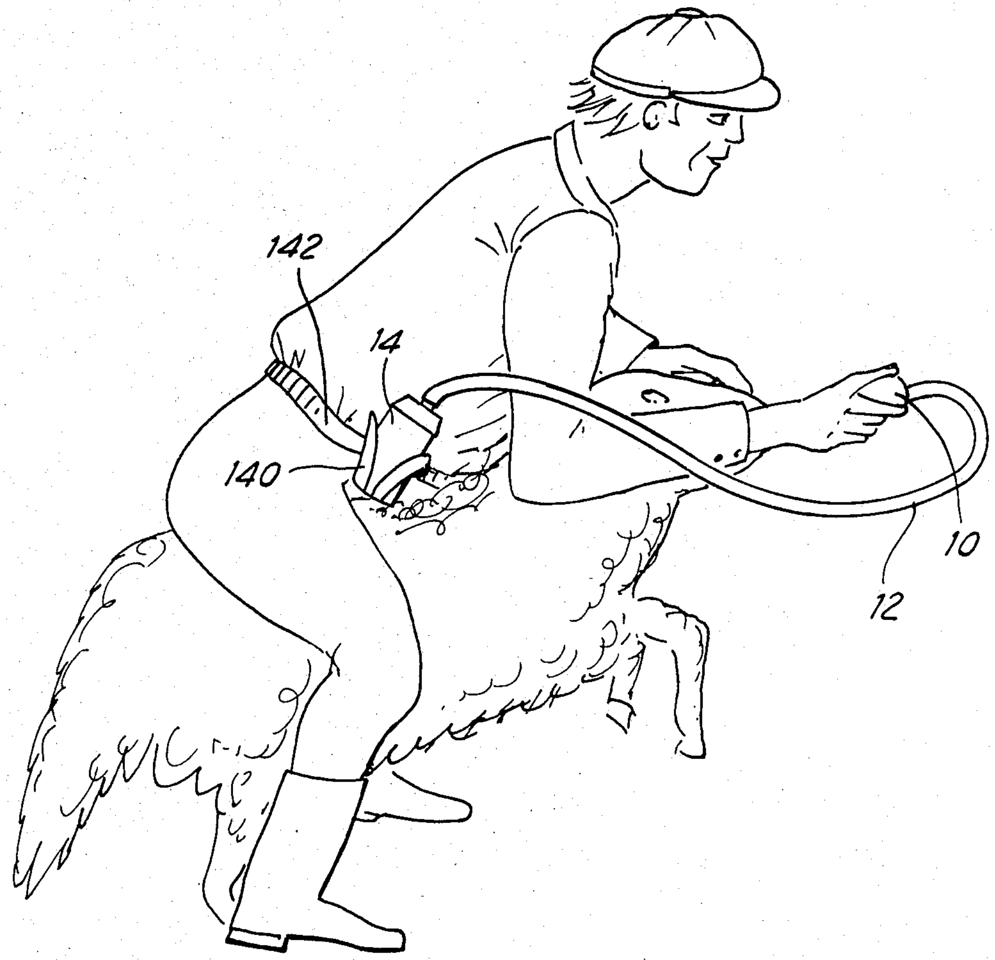

The invention will now be described, by way of example with reference to the accompanying drawings, in which:

FIG. 1 is a perspective view of a gun forming part of apparatus in accordance with the invention, FIG. 2 is a vertical section through the handle and cartridge assembly of the gun, FIG. 3 is a section on line III—III of FIG. 2, FIG. 4 is a rear elevation of a cartridge for use in the gun, FIG. 5 is a section, to a larger scale, on line V—V of FIG. 4, FIG. 6 is a front elevation of the cartridge, FIG. 7 is a plan view of the barrel of the gun, FIG. 8 is a section on line VIII—VIII of FIG. 7, FIG. 9 is an end elevation of the barrel, FIG. 10 is a diagrammatic vertical section through the head of a sheep, showing the barrel of the gun in position in the sheep's mouth, FIG. 11 illustrates the use of the apparatus in administering a capsule to a sheep, FIG. 12 is a horizontal section through the barrel of an alternative embodiment of the invention, and FIG. 13 is a section on line XIII—XIII of FIG. 12.

Referring to the drawings, apparatus for the oral administration of capsules to animals comprises a hand-held gun 10 connected through a flexible tube 12 to a source 14 of pressured gas.

The gun 10 comprises a cartridge housing 16 for holding a replaceable cartridge 18 containing capsules 20, a barrel 22 through which capsules are delivered from the cartridge, and a handle 24 including a trigger 26 which actuates a valve 28 controlling the supply of gas to propel capsules from the cartridge 18, and also actuates an indexing mechanism to rotate the cartridge into position before each discharge.

The cartridge 18 consists of a rotatable member in the form of a disc 30 having a control boss 32 and an annular portion 34 containing a number of equally spaced bores 36, each containing one of the capsules 20. Each bore is closed at one end except for a small hole 38 through which propellant gas can pass. The other end of each bore is closed by a cover 42 which is connected to the member 30 so that the member 30 can rotate relative to the cover. The two components are connected by a snap fitting 44 which enables the components to be easily assembled after capsules 20 have been inserted into the bores 36. The cover 42 has a single hole 46 with which each bore 38 can be aligned in turn. The cover 42 is formed on its outer face with two locating ribs 46 and a ribbed grip portion 48 between the ribs. The outer face of the rotatable member 30 is formed with a ring of teeth 50, equal in number to the bores 36, by means of which the cartridge is indexed as described below.

The cartridge housing 16 comprises a rear plate 52 and a front plate 54 joined by curved side pieces 56. The cartridge 18 fits between the front and rear plates, the opposite ends of the boss 32 fitting into recesses 58 and 60 so that the rotatable member 30 of the cartridge can rotate in the housing. The recess 60 is formed in a tongue 62 formed part of the front plate 54, and the resilience of the material allows the tongue 62 to be pulled forwards to enable the cartridge to be removed from the housing, and a fresh cartridge to be snapped into place. The locating ribs 46 on the cartridge cover 42 engage the sides of an opening 64 in the lower part of the front plate 54, to hold the cover against rotation, and the grip portion 48 is exposed by the opening 64 to facilitate removal of the cartridge.

When the cartridge 18 is in position, the hole 46 in the cartridge cover 42 is aligned with the bore 100 in the barrel 22.

The valve 28 in the handle 24 comprises a cylindrical valve body 70 having an inlet 72 connected to the flexible tube 12, and an outlet 74, which is connected by a tube 76 to a hole 64 in a wall 66 forming part of the rear wall 52 of the cartridge housing. The hole 64 is aligned with the hole 46 and the barrel 22. A valve member 78 having two annular recesses 80 and 82 is movable in the valve body 70 between a lower position, as shown in FIG. 2, and an upper position. In the lower position, to which the valve member 78 is biased by a compression spring 84, the upper recess is in communication with the inlet 72 but isolated from the outlet 74, so that pressurized gas from the source 14 can fill the recess. In the upper position of the valve body 78, the upper recess 80 is isolated from the inlet 72 and is in communication with the outlet 74, so that gas in the recess 80 can expand through the tube 76 to the hole 64 and into the adjacent bore 36 of the cartridge 18. In this position the inlet 72 is in communication with the lower recess 72 and is thus effectively closed. The valve member 78 is moved to the upper position by actuation of the trigger 26 which is slidable in the handle and engages the bottom of the valve member.

The trigger 26 also actuates the cartridge indexing mechanism, which includes a lever 90 pivoted in the handle 24 and connected at one end to the trigger through a compression spring 92. Pivoted to the other end of the lever 90 is a pawl 94 which is spring-biased into engagement with the teeth 50 on the rotatable member 30 of the cartridge 18. On movement of the trigger 26, the lever 90 is pivoted to move the pawl 94 downwards to engage one of the teeth 50 to rotate the member 30 through an angle corresponding to the separation between the bores 36 housing the capsules 20, the pawl riding over the tooth when the trigger is released. A suitable detent mechanism, for example a spring loaded detent (not shown) engaging in successive ones of the holes 38 in the rotatable member 30, is provided to ensure that the rotatable member takes up a position with one of the bores 36 accurately aligned with the bore 100 in the barrel 22 after each indexing rotation.

The valve 28 and indexing mechanism are arranged so that on movement of the trigger 26 the cartridge is rotated by the indexing mechanism before the pressurised gas is supplied from the valve to propel a capsule 20 from the bore 36 aligned with the barrel.

The handle 24 and cartridge housing 16 are made from plastics material, and may conveniently be made in two halves, separated by the vertical plane on which the cross-section of FIG. 2 is taken, joined together by screws.

The barrel 22 comprises a rigid tubular member of plastics having a straight axial bore 100 of uniform cross-section and of diameter slightly greater than that of the capsules 20. The barrel is secured to the body of the gun 10 by clamp members 98 which engage a rear portion 104 of the barrel between two flanges 106 and 108. The cover 42 of cartridge 18 lies against the rear flange 106, with the hole 46 aligned with the bore 100. The bore 100 is slightly flared at its rear end, to facilitate movement of capsules into the bore.

At its foward end the barrel 22 is divided into two similar tip portions 110 which are spaced laterally from one another. Each tip portion curves forwards and downwards from the remainder of the barrel and tapers to a rounded end 112. The shape of the tip portions is such that the upper face of the barrel 22 has a convex shape 114 at its forward end. The lower faces 116 of the tip portions 110 have concave shape, and this concave curve continues rearwards some way into the tubular part of the barrel to give a concave form 118. In the region adjacent this concave form 118, the tubular part of the barrel is formed with a second concave depression 120. The concave forms 118 and 120 are shaped so as to control the movement of the sheep's tongue when the barrel is inserted into its mouth, as described below, whilst the convex curve 114 at the tip is shaped to contact the soft palate and encourage a swallowing reaction. The space between the two tip portions 110 provides a cavity in which a capsule 20 can be deposited at the root of the tongue.

Mounted on the barrel 22 is a shroud 130, which acts to limit the extent to which the barrel can be inserted into the mouth of the animal. The position of the shroud 130 is adjustable axially, the shroud being held in position by a bead 132 on the shroud engaging snapwise into one of a series of recesses 128 in the barrel, to enable the same gun to be used for different types of animal, for example sheep, lambs and calves.

The source 14 of pressurised gas to which the flexible tube is connected may be a canister supplying an inert non-toxic gas; for example of the type used to administer liquid respiratory drugs. The canister may be replaceably held in a holster 140 secured by a belt 142 or harness to the user's body so that the user has both hands free to hold the sheep and manipulate the gun.

In use of the apparatus, a cartridge 18 containing capsules 20 is inserted into the cartridge housing 16 of the gun 10 and the gun is connected to the source 14 of pressurized gas. The sheep to be dosed is held, for example by gripping the sheep's body between the user's legs, as shown in FIG. 11, so that the user can hold the sheep's jaw with one hand and the gun 10 with the other hand. The barrel 22 is inserted into the sheep's mouth. As the barrel 22 is inserted, the convex upper faces 114 of the tip portions 110 follow the hard palate 150 until they engage the soft palate 152, as shown in FIG. 10. The soft palate is moved from the broken line position shown in FIG. 10, to open the oesophagus and to form a space into which a capsule 20 can be deposited. The engagement of the soft palate also causes a swallowing reaction. The lower surface of the barrel engages the animal's tongue, the concave form 120 engaging the front part 154 of the tongue and the concave form 118 beneath the tip of the barrel 22 engaging the dorsum 156. This controls the tongue, preventing it from moving to the normal position, shown in broken lines in FIG. 10, in which the tongue and dorsum lie closely against the hard palate 150. The shape of the lower surface of the barrel also has the effect of encouraging the tongue to move forward, to help form a space at the base of the dorsum. The fork-like end of the barrel 22 formed by the spaced tip portions 110 prevent the soft tissues of the soft palate and the dorsum from collapsing around the mouth of the barrel 22 and so preventing the capsule escaping from the barrel. The position of the shroud 130 ensures that the tip of the barrel 22 is at the appropriate position in the animal's mouth.

After the barrel 22 has been inserted, the operator presses the trigger 26, which rotates the cartridge 18 to move a capsule 20 into the firing position as shown in FIG. 1, and then releases a metered volume of pressurized gas from the valve 28 as described above. The gas passes through the holes 64 and 38 and propels the capsule 20 from its recess 36 in the cartridge into the bore 100 of barrel 22 and along the bore until it reaches the space between the tip portions 110. The capsule is thus deposited into the animal's mouth and is swallowed. The barrel 22 is then withdrawn, and is immediately ready to be used for the next animal.

The apparatus thus enables capsules to be administered to sheep rapidly, without risk of causing damage or undue distress to the sheep. The apparatus is very light and portable, and is relatively simple and cheap to manufacture.

The cartridge 18 may be supplied in disposable form, the cartridges being filled with capsules by the manufacturer and supplied to the customer who can simply replace a spent cartridge with a full one, thus saving time in use of the apparatus.

The dimensions of the barrel will depend on the animal for which the apparatus is to be used. For example, the following approximate dimensions have been found to be suitable for the barrel shown in FIGS. 7 and 8, for use with sheep, lambs and calves. The barrel 22 has an overall length of about 260 mm, the distance between the shroud 130 and the end 112 of the barrel being adjustable between about 195 mm and 105 mm depending upon the position of the shroud. The tip portions 110 have an axial length of 40 mm measured from the end 122 of the tubular portion of the barrel. The convex curve 114 at the tip of the barrel has a radius of curvature of 74 mm, with a centre of curvature positioned 54 mm, measured axially, from the extreme end 112 of the barrel, the curve 114 extending 54 mm from the end 112. The forwardmost concave curve 118 has a radius of curvature of 66 mm, on a centre of curvature spaced 41 mm from the end 112, and extends 60 mm from the end 112. The second concave curve 120 also has a radius of curvature of 66 mm, on a centre of curvature spaced 79 mm from the end 112, and has an axial extent of 35 mm. The barrel 22 has an outside diameter of 20 mm and a bore of diameter 8.6 mm. The gap between the opposed faces 124 of the tip portions 110 is 10 mm, each tip portion having a thickness of approximately 5 mm.

Instead of providing a single gun with an adjustable shroud, it is possible to provide a separate gun for each type of animal, with the barrel having the appropriate length. The shroud could then be fixed in position, or omitted entirely.

For larger animals, such as cattle, the shape of the tip of the barrel may be modified. For example, FIGS. 12 and 13 show a barrel 200 in which the tip portions 210 are provided with rounded extensions 212 and 214 on their upper and lower faces. In addition, the two concave forms of the previously described embodiment are replaced with a single, larger concave form 216 on the underside of the tip of the barrel, designed to control the tongue of the larger animal.

It will be appreciated that other modifications could be made in the described embodiment. For example, other forms of cartridge or magazine to hold the capsules could be used. Other sources of pressurized gas or air, such as a compressor, could be used. Instead of using gas or air as a propellant, other means of moving the capsules to the tip of the barrel could be used, for example a rod or piston movable in the tube to push the capsules along it.

I claim:

1. Apparatus for the oral administration of capsules to animals, comprising a tubular member having a tip and having a length such that when inserted into the animal's mouth the tubular member extends above the animal's tongue, said tubular member having a lower contact surface which engages the animal's tongue to hold the same in position, and said tip having an upper contact surface forwardly of the lower contact surface which engages the soft palate near the root of the animal's tongue to initiate swallowing, means for introducing a capsule into the tubular member rearwardly of the tip, in which the tip consists of two tip portions extending from the mouth of the tubular member and laterally spaced from one another so as to define a cavity in which a capsule is deposited at the root of the animal's tongue.

2. Apparatus as claimed in claim 1, in which the upper contact surface is convexly curved.

3. Apparatus as claimed in claim 2, in which the lower contact surface is shaped in a concave curve and adapted to engage the dorsum of the animal's tongue to restrain movement of the dorsum.

4. Apparatus as claimed in claim 1 in which the lower contact surface is shaped in a concave curve and adapted to engage the dorsum of the animal's tongue to restrain movement of the dorsum.

5. Apparatus as claimed in claim 1, in which the means for introducing a capsule along the tubular member to its tip includes means for applying air or gas under pressure to the tubular member.

6. Apparatus as claimed in claim 5, in which the tubular member is part of a hand-held gun including a handle and a magazine to hold one or more capsules in a position in which they can be inserted into the tubular member.

7. Apparatus as claimed in claim 6, in which the gun is connected to a source of pressurizing gas through a flexible tube, and the gun includes a manually operated valve means operable to allow gas to be supplied to the tubular member.

8. Apparatus as claimed in claim 7, in which the valve means is operable to supply a metered amount of gas to the tubular member.

9. Apparatus as claimed in claim 7 or claim 8, in which the source of pressurizing gas is a container carried by a belt or harness adapted to be secured to the user's body.

10. Apparatus as claimed in claim 8, in which the source of pressurizing gas is a container carried by a belt or harness adapted to be secured to the user's body.

11. Apparatus as claimed in any one of claims 6 to 9, in which the magazine includes a cartridge replaceably mounted in a housing forming part of the gun, the cartridge including a rotatable member having a number of circumferentially spaced cavities each adapted to house one capsule, and the rotable member being rotatable in the housing so that each cavity can be moved in succession to a position in which it can be moved into the tubular member.

12. Apparatus as claimed in claim 11, in which there are provided actuating means operable manually both to rotate the rotatable member of the housing and to operate valve means to supply pressurized gas to the tubular member.

13. Apparatus as claimed in claim 7, in which the magazine includes a cartridge replaceably mounted in a housing forming part of the gun, the cartridge including a rotatable member having a number of circumferentially spaced cavities each adapted to house one capsule, and the rotatable member being rotatable in the housing so that each cavity can be moved in succession to a position in which it can be moved into the tubular member.

14. Apparatus as claimed in claim 8, in which the magazine includes a cartridge replaceably mounted in a housing forming part of the gun, the cartridge including a rotatable member having a number of circumferentially spaced cavities each adapted to house one capsule, and the rotatable member being rotatable in the housing so that each cavity can be moved in succession to a position in which it can be moved into the tubular member.

15. Apparatus as claimed in claim 14, in which there are provided actuating means operable manually both to rotate the rotatable member of the housing and to operate valve means to supply pressurized gas to the tubular member.

16. Apparatus as claimed in claim 9, in which the magazine includes a cartridge replaceably mounted in a housing forming part of the gun, the cartridge including a rotatable member having a number of circumferentially spaced cavities each adapted to house one capsule, and the rotatable member being rotatable in the housing so that each cavity can be moved in succession to a position in which it can be moved into the tubular member.

17. Apparatus as claimed in claim 16, in which there are provided actuating means operable manually both to rotate the rotatable member of the housing and to operate valve means to supply pressurized gas to the tubular member.

18. Apparatus as claimed in claim 13, in which there are provided actuating means operable manually both to rotate the rotatable member of the housing and to operate valve means to supply pressurized gas to the tubular member.

19. Apparatus for the oral administration of capsules to animals, comprising a tubular member adapted to be inserted into the animal's mouth so that the tip of the tubular member is near the root of the animal's tongue, means for introducing a capsule into the tubular member and for propelling the capsule to its tip, the tip of the tubular member consisting of two tip portions extending from the mouth of the tubluar member and laterally spaced from one another so as to define a cavity in which a capsule is deposited at the root of the animal's tongue, the tubular member being formed at or near its tip with a convexly curved upper surface adapted to engage the animal's soft palate to encourage a swallowing reaction, and the lower surface of the tubular member at or near its tip having a first concave portion adapted to engage the dorsum of the animal's tongue to restrain movement of the dorsum and a second concave portion adjacent to the first concave portion and adapted to engage and restrain movement of the animal's tongue.

* * * * *